United States Patent [19]
Pittaro

[11] 4,437,332
[45] Mar. 20, 1984

[54] ULTRASONIC THICKNESS MEASURING INSTRUMENT

[75] Inventor: Richard J. Pittaro, West Redding, Conn.

[73] Assignee: Krautkramer-Branson, Inc., Lewistown, Pa.

[21] Appl. No.: 429,127

[22] Filed: Sep. 30, 1982

[51] Int. Cl.³ ............................................. G01N 29/00
[52] U.S. Cl. .................... 73/1 DV; 73/597; 73/615; 73/624; 73/627; 73/644
[58] Field of Search ............ 73/1 DV, 597, 614, 615, 73/616, 617, 624, 627, 644

[56] References Cited
U.S. PATENT DOCUMENTS 3,554,013  1/1971  Berg ........................................ 73/615
3,918,296  11/1975  Kitada .................................... 73/627

FOREIGN PATENT DOCUMENTS 657338  4/1979  U.S.S.R. ................................ 73/644

*Primary Examiner*—Howard A. Birmiel
*Attorney, Agent, or Firm*—Ervin B. Steinberg; Philip J. Feig

[57] ABSTRACT

A programmable ultrasonic thickness and acoustic velocity measuring instrument is provided which includes automatic zeroing (calibrating) means, automatic temperature compensation and high temperature warning means, automatic probe identification means, means for automatically correcting the measurement readings for probe characteristics, means for storing and displaying of the minimum wall thickness during a predetermined time interval, and means for providing a display indicative of the difference between a measured thickness and a preprogrammed value.

12 Claims, 5 Drawing Figures

ULTRASONIC THICKNESS MEASURING INSTRUMENT

BACKGROUND OF THE INVENTION

This invention relates to ultrasonic thickness and acoustic velocity measuring instruments. More specifically, this invention refers to an ultrasonic measuring instrument for determining the thickness of a workpiece, the instrument including automatic zeroing (calibrating) means, automatic temperature compensation and high temperature warning means, automatic identification means of the probe, means for correcting the measurement readings for probe characteristics, means for storing and displaying of the minimum wall thickness during a predetermined time interval, and means for providing a display indicative of the difference between a measured thickness and a preprogrammed value.

It is well known in pulse-echo ultrasonic thickness measuring that ultrasonic energy transmitted into a workpiece is reflected at a defect or other acoustic discontinuity, such as the entrant surface or rear wall. By measuring the time of travel of the ultrasonic energy signal through a workpiece of known acoustic velocity, i.e. from the time the ultrasonic energy enters the workpiece until a rear wall echo signal is received, the thickness of the workpiece can be determined. Conversely, if the thickness of a workpiece is known, the acoustic velocity can be determined.

Some ultrasonic probes, particularly those used in corrosion testing of plates or pipes, are dual-element probes, also referred to as "pitch-catch" probes. These probes are used because of the rough rear surfaces encountered during corrosion testing.

The piezoelectric transducer elements associated with dual probes typically are mounted on blocks of heat insulating coupling means, also referred to as delay lines, which are usually constructed of polymeric thermoplastic material. The probe elements, coupled to respective delay lines, are inclined at a predetermined angle with respect to the entrant surface of a workpiece. The transmit element is coupled to a first delay line and the receive element is coupled to a second delay line, both delay lines being of the same material. The two delay lines are electrically and acoustically isolated by an acoustic barrier, such as cork, and the entire assembly is enclosed in a probe housing.

In the present invention, the transmit element, which also acts as a receive element, is mounted on a first delay line which is longer than the delay line upon which the receive element is mounted. In addition, the delay line coupled to the transmit element contains an artificial reflector, for instance, a transversely drilled notch. The notch is located at a distance "X" from the front face of the delay line. The delay line upon which the receive element is mounted is dimensioned to be shorter than the first delay line by a distance "2X." The transmit/receive element measures the time for an ultrasonic signal transmitted by the transmit element to reach the notch whereat the signal is reflected and returns to the same element. This measured time is used to identify a specific probe type. If the delay line is characterized by a length L, the round trip distance traveled by the notch reflected ultrasonic signal in the delay line is $2(L-X)$.

After determining the probe type used by means of the notch reflected echo signal, preprogrammed probe characteristic factors are retrieved from a PROM of a microprocessor contained in the instrument. The calibration factors include correction for path length errors due to the angle of incidence of the transmit signal and echo signal. Retrieval of the proper values is assured since the measured notch reflected echo signal is different for each probe type. The use of preprogrammed memory for providing probe compensation data in an ultrasonic pulse-echo instrument is described, for example, in U.S. Pat. No. 4,102,205, issued to W. Pies et al., entitled "Method and Apparatus for Ultrasonic Nondestructive Testing of Workpieces with Automatic Compensation for the Probe, Workpiece Material, and Temperature," dated July 25, 1978.

Having identified the probe type used, the instrument is calibrated by coupling a dual-element probe to a workpiece of known thickness T. The path length of a rear wall reflected ultrasonic signal transmitted from the transmit element through the delay line and workpiece to the rear wall and back to the receive probe is $2L-2X+2T$. By subtracting the transit time of the notch reflected signal from the transit time of the rear wall reflected signal, and adjusting for the angle of incidence of the ultrasonic energy signals, the instrument will be calibrated by virtue of an evaluation unit calculating a required offset value in order to display the known thickness T. In addition to being calibrated, the instrument is thereafter automatically temperature compensated for variations of the transit time of signals traveling through the delay lines due to thermal effects. Moreover, if the notch reflected signal transit time changes by more than a predetermined value, the probe is becoming too hot. The instrument provides a warning of this condition to an operator prior to the probe being damaged. In prior U.S. Pat. No. 4,182,155 issued to K. A. Fowler, entitled "Method and Apparatus for Zero Point Calibration of Ultrasonic Thickness Gauge" dated Jan. 8, 1980, a dual-element probe having delay lines of different lengths for calibrating an ultrasonic thickness gauge is described. In the Fowler patent, prior adjustment of the instrument using a gauge block is required for calibration whereas in the present invention calibration is performed automatically by the instrument.

Another improvement of the present invention resides in the automatic activation feature. A calibration specimen is provided on the face of the instrument. Coupled to the calibration specimen is a receive probe. When the instrument is in the off condition, periodic monitoring of the receive probe is performed. The microprocessor contains C-MOS circuitry which when the instrument is in the off condition operates at a low pulse repetition frequency for minimizing the power consumption. If the receive probe detects several ultrasonic signals passing through the calibration block, the unit is activated.

When the instrument is activated, the probe type is automatically identified, and the microprocessor calculates a zeroing offset value for causing the readout to display the known thickness of the calibration block. Both the thickness and the acoustic velocity of the specimen are known and permanently stored in the instrument memory. The calculated offset signal zeroizes the instrument and is used in all subsequent measurements. This means of calibrating the instrument is an alternative to the use of an external workpiece of known thickness and acoustic velocity for calibration.

In addition, in a store mode the instrument using either hardware or software, retains the minimum thickness measurement display for a predetermined time interval, usually for several seconds. In thickness testing of corroded workpieces, while the probe scans the workpiece surface, the minimum thickness measurement is often calculated and displayed faster than the operator can make an observation. Storage and display of the minimum thickness for several seconds allows the operator to observe the minimum reading measured during the time interval and note the area tested. The operator can then rescan the workpiece to find the exact location of the minimum reading or perform other corrective action to the workpiece.

The instrument also is programmed to display a difference thickness reading. That is, instead of displaying the true measured thickness, the readout will display the difference between the measured signal and a predetermined nominal value. This feature is particularly useful in quality control applications.

Further and still other provisions of the present invention will become more clearly apparent when the following specification is read in conjunction with the accompanying drawings.

DETAILED DESCRIPTION OF THE INVENTION

Figure 1:
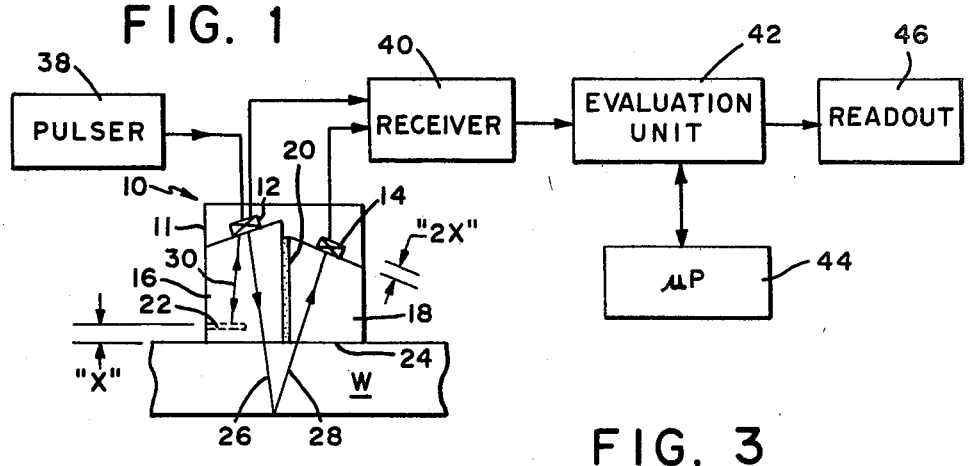
FIG. 1 is a schematic block diagram of a preferred embodiment of the invention using a dual-element probe.

Referring to the figures and FIG. 1 in particular, there is shown a schematic block diagram of the present invention. A dual-element probe 10 comprising a transmit-receive piezoelectric element 12 and a receive element 14 is acoustically coupled to the entrant surface of a workpiece for transmitting an ultrasonic energy signal into the workpiece W and receiving echo signals therefrom.

The element 12 is coupled to a coupling means or delay line 16 and the element 14 is coupled to a delay line 18. Both delay lines are of the same plastic material e.g. Lucite, and are acoustically isolated from each other by a sound absorbing barrier 20, such as cork. The entire assembly is disposed in a housing 11.

Delay line 16 includes a transversely drilled notch 22 disposed at a distance "X" from the front surface 24 of the probe 10. The length of the delay line 18 is dimensioned to be a distance "2X" shorter than the length of the delay line 16. The distance "X" is made different for each probe type. Differences in probe type are based upon such factors as the frequency of the ultrasonic energy signal, the angle of the elements 12 and 14 relative to an axis normal to the workpiece entrant surface, maximum permissible operating temperature of the probe 10, the length L of the delay line, and the like. The characteristics of each probe type are stored in a memory contained in the instrument and are recalled for use when measuring workpiece thickness as will be described herein.

In pulse-echo ultrasonic thickness measurement, responsive to a transmit pulse from pulser 38 an ultrasonic search signal is transmitted by the element 12 through delay line 16 into the workpiece. Upon intercepting an acoustic discontinuity, a portion of the transmitted signal is reflected back through the workpiece and delay line 18 to the receive element 14.

The received ultrasonic echo signals are converted by the element 14 into electrical signals and are provided to a receiver 40. The echo responsive electrical signals which are manifest at the output of the receiver 40 are provided to an evaluation circuit 42 for calculating workpiece properties, such as the workpiece thickness or acoustic velocity. The workpiece thickness is the product of the acoustic velocity of the workpiece multiplied by one-half the transit time of the ultrasonic signal traveling through the workpiece W.

The transit time of the ultrasonic signal traveling through the workpiece is commonly determined by measuring the time from receipt of the entrant surface responsive echo signal to the time of receipt of a rear wall responsive echo signal, see U.S. Pat. No. 3,486,368 dated Dec. 30, 1969 issued to Kilian H. Brech and entitled "Ultrasonic Inspection Apparatus." Alternatively, a start measurement signal can be electrically generated to coincide with the time at which an entrant surface echo responsive signal would be received by receive probe 14, see U.S. Pat. No. 3,427,866 dated Feb. 18, 1969 issued to F. G. Weighart entitled "Ultrasonic Thickness Gauge and Flaw Detector." Both of these and other techniques for measuring workpiece thickness and acoustic velocity are well known in the art.

Since a dual-element probe is used, geometric correction of the measured transit time is required in order to compensate for the angle of the "V"-shaped signal path. By way of contrast, when using a single element probe, the ultrasonic signal is usually transmitted into the workpiece in a direction normal to the entrant surface and to the rear wall of the workpiece. In the latter case, geometric correction is not required. In order to provide the proper geometric compensation when using a dual-element probe, the evaluation circuit 42 is controlled by a microprocessor 44 which includes a PROM preprogrammed with the characteristics of each probe type intended to be used with the instrument. If a nonrecognized probe 10 is used, the PROM contains general correction data for providing an average probe compensation, and conventional zeroing and calibrating techniques are used.

The probe type identification is determined by measuring the distance from the transmit element 12 to the notch 22. When transmitting a search signal into the workpiece, a portion of the ultrasonic energy signal transmitted from transmit element 12 is reflected at notch 22 back toward the element 12. The transit time of the notch reflected echo signal is measured by the evaluation unit 42 and the microprocessor 44 recognizes the measured transit time as a particular probe type. When the probe type is identified, the proper probe characteristic compensation values are provided from the PROM in microprocessor 44 to the evaluation unit 42 for use in performing the subsequent thickness or acoustic velocity measurements.

The receiver 40 includes a stepped gain function for the purpose of confirming receipt of a notch signal. After a notch reflected signal is received, the gain of the receiver 40 is decreased in order to facilitate detection of the receipt of an entrant surface signal. In this manner the instrument confirms that a notch reflected signal has been received and not an entrant surface echo signal. The use of stepped or variable gain receiver circuits in ultrasonic non-destructive measurements is described, for example, in U.S. Pat. No. 4,050,292 issued to P. K. Bloch, entitled "Method and Apparatus for Testing Railroad Wheels," dated Sept. 27, 1977.

Once the probe correction values for the notched probe have been fed into the evaluation unit 42, in order to provide automatic temperature compensation for the probe 10, the transit time of the ultrasonic signal from element 12 to the notch 22 and back to the element 12 along path 30 is measured and stored in memory. The probe 10 is then coupled to a workpiece of known thickness T and known acoustic velocity V. An ultrasonic signal is transmitted from the transmit element 12 though delay line 16 via path 26 to the rear wall of the workpiece where the signal is reflected and travels along path 28 through delay line 18 to the receive element 14.

The path length of the notch reflected signal along path 30, assuming that the length of delay line 16 is L, is:

$$2(L-X) = 2L - 2X. \quad (Eq. 1)$$

The path length in delay lines 16 and 18 of the signal traveling along paths 26 and 28 is:

$$L + L - 2X = 2L - 2X. \quad (Eq. 2)$$

The latter value is measured by measuring the time from the transmission of the transmit signal by the element 12 until the receipt of the rear wall responsive echo signal by element 14 and subtracting twice the known workpiece thickness T suitably compensated for the probe type used.

The values measured by equation (1) and equation (2) are equal and should remain equal for all measurements. Therefore, in subsequent thickness measurements of unknown workpiece thicknesses, the "notch signal," i.e. the transit time of the ultrasonic signal from element 12 to reflection at the notch 22 and return to element 12 sets a flip-flop and the echo responsive signal from the workpiece rear wall resets the flip-flop. The width of the output signal of the flip-flop, which is automatically probe temperature compensated, is responsive to the workpiece thickness. The measuring of the pulse width of an output signal from a timing flip-flop (measuring time interval) in ultrasonic measuring instruments is well known. Proper geometric and zeroing corrections are provided for measuring the workpiece thickness. During subsequent measurements, the evaluation unit 42 compares the initially measured notch reflected transit time value with subsequently measured notch reflected transit time values to determine thermal effects upon the delay lines. If a subsequently measured value of the notch reflected signal travelling along path 30 varies by more than a predetermined amount from the initially measured value, the probe 10 is becoming too hot. In such an event, a warning signal, such as illumination of indicator 41, is provided to the operator so that further testing may cease before damage to the probe 10 results. The temperature compensation scheme of setting the timing flip-flop with the notch reflected echo signals and ending the timing flip-flop with resetting by the rear wall reflected signals is accurate so long as the probe front surface 24 wears evenly along the entire surface so that the differences in delay line path length within coupling members 16 and 18 remains equal to 2X.

If the instrument fails to detect the sequence of a notch reflected signal and an entrant surface echo signal, an assumption is made that a notched probe is not being used, but rather that a "special" probe is used and indicator 43 is illuminated. The PROM has stored in its memory so-called average geometric correction factors which are provided to the evaluation unit 42. When average geometric corrective factors are used, the conventional instrument calibration technique using a test block with stepped thicknesses is required to zeroize and calibrate the instrument. The correction values determined by the conventional means are then stored in the microprocessor 44 for use in performing subsequent thickness or acoustic velocity measurements.

Figure 2:
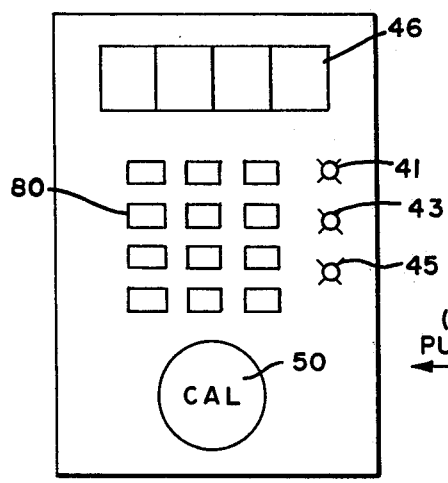
FIG. 2 is a front view of the instrument.
Figure 3:
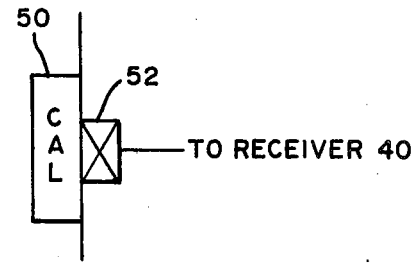
FIG. 3 is a sectional view of the calibration specimen and receive probe.

The present instrument also includes a novel activation means. On the face of the instrument there is disposed a calibration specimen 50 of known thickness and acoustic velocity as shown in FIG. 2. With reference to FIG. 3, a receive probe 52 is permanently coupled to one side of the specimen 50. In normal testing the instrument operates with a high frequency clock having a typical frequency of 2 MHz. When the instrument is inactive, the instrument is controlled by a low frequency clock having a typical frequency of 1 KHz. The microprocessor 44 and evaluation unit 42 comprise C-MOS low power components to minimize battery power consumption. Periodically, typically at half second intervals, the output of probe 52 is monitored to determine the receipt of an ultrasonic signal. If no signal is received, the unit remains off. When a signal is received, the time interval between a transmit pulse from pulser 38 to the receipt of a signal by receive probe 52 is measured. If several measurements indicate that the time interval is equal to the time of travel of a through-transmission ultrasonic signal from probe 10 through specimen 50 to probe 52, the instrument becomes activated. The probe 10 type is determined, the high frequency clock is activated and the instrument is ready for use.

The turn on procedure also activates the automatic zeroing function of the instrument. When a signal is received by the probe 52, the instrument is measuring the thickness of the specimen 50 of the known thickness, the acoustic velocity value of which is stored in the microprocessor 44. Automatic apparatus zeroing is achieved by calculating an offset time (zero compensation) using the following through-transmission equation:

Known thickness of specimen 50 = known acoustic
velocity of specimen × (measured transit
time + offset time)          (Eq. 3)

In the preferred embodiment, the thickness and the acoustic velocity of the specimen 50 are permanently stored in the memory of the PROM contained in microprocessor 44. The measured pulse-echo transit time of the signal measuring the thickness of specimen 50 is calculated by evaluation unit 42. Since the probe type has already been determined, suitable geometric corrections are factored into the thickness measurement. Using the measured transit time for several cycles in order to assure proper coupling of the probe 10 to the specimen 50 and to assure that ambient thermal equilibrium has been achieved, the equation (3) is solved for the offset time (zeroing correction). The calculated offset time value is stored in the memory of microprocessor 44 as an automatic zeroing offset for all subsequent measurements using the probe and instrument until recalibration. It is also possible to zero (calibrate) the instrument by means of a workpiece of known thickness and acoustic velocity. The known thickness and acoustic velocity values are entered into the memory of the microprocessor 44 by means of a keyboard 80 or other control. The probe type is identified and equation (3) is solved for the offset time using the programmed workpiece thickness and acoustic velocity. The instrument is now ready for pulse-echo ultrasonic thickness measurement using the specific probe and instrument. Geometric compensation, zeroing and temperature compensation have been quickly and automatically achieved.

When testing workpieces of unknown thickness, the acoustic velocity of the workpiece W to be measured is entered by means of the keyboard 80 or other control on the instrument into the memory of the microprocessor 44. The offset (zeroing) value which was calculated during the turn on procedure is recalled from memory, and the proper PROM probe type correction has been identified. Therefore, the workpiece thickness measurement is determined by solving the equation:

workpiece thickness = acoustic velocity of
workpiece programmed into
microprocessor × (pulse-echo transit time + offset
time + geometric compensation).          (Eq. 4)

Conversely, if it is desired to measure the acoustic velocity of workpieces, the known thickness of the workpiece is programmed into the microprocessor 44 and equation (4) is solved for the unknown acoustic velocity.

Figure 4:
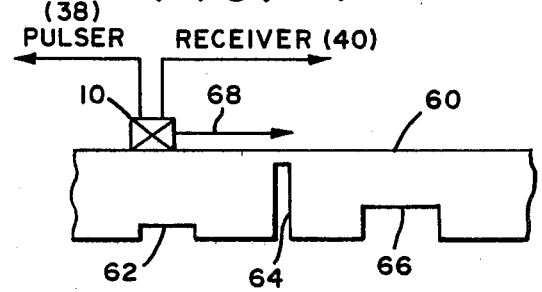
FIG. 4 is a representation of a probe scanning a corroded workpiece.
Figure 5:
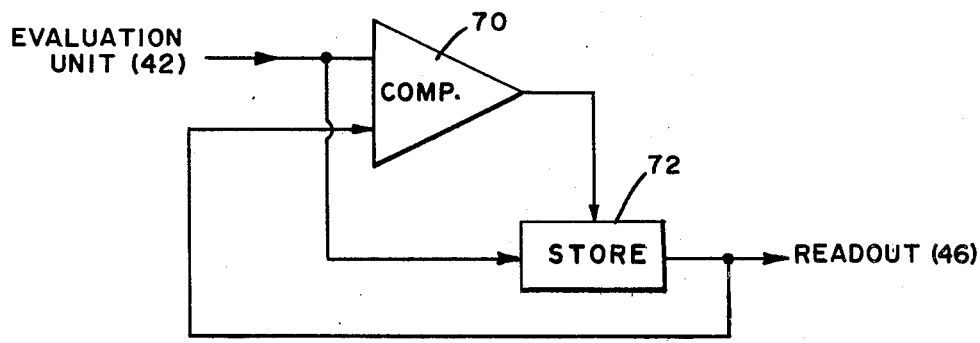
FIG. 5 is a schematic diagram of a minimum value detector.

In one embodiment of the instrument, a minimum thickness storage feature is included. As best seen in FIG. 4, the probe 10 during testing is caused to traverse the surface 60 of a corroded workpiece. In FIG. 4, the workpiece shown in section contains three defects 62, 64 and 66 of different width and depth. The most critical defect is defect 64 due to the fact that the remaining workpiece thickness between the defect 64 and surface 60 is the minimum. As the probe 10 traverses the workpiece, left to right in the direction of arrow 68, the workpiece thickness is continuously measured and provided as an input to comparator 70 in FIG. 5 and to the input of a storage means 72. The other input of comparator 70 is connected to the output of storage means 72. The output of storage means 72 is also provided to the readout 46 for displaying the lowest thickness measurement. FIG. 5 is a simplified schematic block diagram with suitable buffer and latching means omitted. As the probe 10 scans the workpiece surface, the new thickness measurement is compared in comparator 70 with the previously stored minimum thickness measurement. If the new measurement is less than the stored value, indicative of a thinner workpiece section, the storage means 72 and hence readout means 46 are updated to the lower measured thickness valve. After a predetermined time interval, typically several seconds, the storage means and readout is reset (by means not shown) and the process resumes for another time interval.

While FIG. 5 illustrates circuit elements for determining and storing a minimum thickness reading, the minimum value calibration may be performed by means of a software program contained in microprocessor 44.

The advantage of storing the minimum thickness reading is to assure that the operator is able to observe and note the minimum thickness of the workpiece region while continuously scanning the workpiece surface 60. If desired, the operator can rescan the workpiece to locate the precise location of the minimum thickness section. Alternatively, based upon the minimum thickness reading observed, corrective action of the workpiece may be performed.

In another variation, the instrument may include an audio or video alarm, such as indicator 45, which alerts the operator to the measurement of a workpiece thickness less than a predetermined minimum value.

In a still further modification of the instrument, the readout 46 is made to display a differential mode thickness, usually for quality control testing. In this mode, a predetermined thickness value is programmed into the microprocessor 44 by means of a keyboard 80. The instrument then measures a differential thickness value, i.e. the difference, greater than or less than, the predetermined nominal thickness value. The measured differential thickness value is displayed. In this manner, by causing an alarm to indicate a differential thickness value greater than a predetermined tolerance range, a workpiece can be rejected or reexamined more closely, as the application demands.

While there has been described and illustrated a preferred embodiment of an ultrasonic thickness measuring instrument and several variations and modifications thereof have been indicated, it will be apparent to those skilled in the art that further and still other modifications and variations can be made without deviating from the broad scope of the invention which shall be limited solely to the claims appended hereto.

What is claimed is:

1. A dual-element ultrasonic probe comprising in combination a pair of elongated plastic coupling means arranged in substantially parallel juxtaposition in slightly spaced acoustically isolated relation, each of said coupling means acting as a delay line for ultrasonic signals passing therethrough between respective oppositely disposed end surfaces, each such coupling means having a respective electroacoustic transducer element coupled to a respective first end surface and the opposite second end surfaces of both coupling means adapted to be coupled for simultaneous acoustic contact with a workpiece, the improvement comprising:
  one of said coupling means characterized by length L having a reflector disposed at a longitudinal distance X from its second end surface for partially reflecting ultrasonic signals transmitted from its respective first end surface disposed transducer element, and
  the other coupling means characterized by length equal to $L - 2X$.

2. A dual-element ultrasonic probe as set forth in claim 1, said pair of coupling means being of the same material.

3. A pulse-echo ultrasonic measuring instrument comprising:
  a first coupling means having a first end and a frontal surface end, the distance between said first end and said frontal surface end being L and further having a reflector disposed therein at a distance X from its frontal surface end;
  a second coupling means having a first end and a frontal surface end, the distance between said first end and said frontal surface end being a distance L−2X;

an acoustical barrier separating said first coupling means and said second coupling means;

a first transducer element coupled to said first end of said first coupling means for transmitting and receiving ultrasonic energy signals;

a second transducer element coupled to said first end of said second coupling means for receiving ultrasonic energy signals;

pulse generating means coupled to said first transducer element for providing a transmit pulse for causing said first element to transmit an ultrasonic search pulse into and through said first coupling means and into a workpiece;

said first transducer element receiving an ultrasonic echo signal reflected from said reflector and converting said echo signal to a first electrical signal;

said second transducer element receiving an ultrasonic echo signal reflected from an acoustic discontinuity in the workpiece and converting said echo signal to a second electrical signal;

receiver means coupled to said first and second transducer elements for receiving said first and second electrical signals and providing respective first and second echo responsive electrical signals responsive thereto;

evaluation means coupled to said receiver means and said pulse generating means for receiving said first and second echo responsive electrical signals and said transmit pulse and calculating properties of the workpiece based upon the receipt of said first and second echo responsive electrical signals;

microprocessor means coupled to said evaluation means for controlling said evaluation means and providing preprogrammed data thereto in order to perform said calculating, and display means coupled to said evaluation means for displaying said property of the workpiece.

4. A pulse-echo ultrasonic measuring instrument as set forth in claim 3, said evaluation means commencing a measuring time interval responsive to said first echo responsive electrical signal and terminating the time interval responsive to said second echo responsive electrical signal, and further providing a probe indicative signal commensurate with the time interval between said transmit pulse and said first echo responsive electrical signal, and said microprocessor means upon receipt of said probe indicative signal providing preprogrammed probe characteristic correction data to said evaluation means.

5. A pulse-echo ultrasonic measuring instrument as set forth in claim 4:

said evaluation means calculating the time interval of said measuring time interval;

said evaluation unit providing an offset time signal required to cause said calculated measuring time interval to be commensurate with a known workpiece thickness, and said evaluation means further providing said calculated offset time signal to said microprocessor means for storing said offset time interval signal for subsequent measurements.

6. A pulse-echo ultrasonic measuring instrument as set forth in claim 4, said microprocessor means storing a first said probe indicative signal and comparing subsequent said probe indicative signals to said first said probe indicative signal for providing a signal indicative of a temperature change of said probe.

7. A pulse-echo ultrasonic measuring instrument as set forth in claim 3, including means for storing and displaying said property of the workpiece for a predetermined time interval.

8. A pulse-echo ultrasonic measuring instrument as set forth in claim 3, including means for programming a predetermined property value of a workpiece in said microprocessor means and further means for causing said readout to display a value indicative of the difference between a measured workpiece property value and said stored value.

9. A pulse-echo ultrasonic measuring instrument as set forth in claim 3, including means for programming a property of a workpiece in said microprocessor means.

10. A pulse-echo ultrasonic measuring instrument as set forth in claim 9, said property of the workpiece being the thickness of the workpiece.

11. A pulse-echo ultrasonic measuring instrument as set forth in claim 9, said property of the workpiece being the acoustic velocity of the workpiece.

12. A pulse-echo ultrasonic measuring instrument as set forth in claim 3 including:

a calibration specimen disposed on the instrument;

a receive probe coupled to one side of said specimen;

means for periodically monitoring said receive probe for the presence of an ultrasonic signal traveling through said specimen, and means for energizing said instrument when said means for monitoring detects an ultrasonic signal.

* * * * *